United States Patent [19]

Samejima et al.

[11] Patent Number: 5,254,347
[45] Date of Patent: Oct. 19, 1993

[54] CONTROLLED RELEASE PHARMACEUTICAL PREPARATION AND METHOD FOR PRODUCING THE SAME

[75] Inventors: Masayoshi Samejima, Mino; Kazuo Noda, Takarazuka; Yoshiyuki Hirakawa, Toyonaka; Hiroyuki Yoshino, Suita, all of Japan

[73] Assignee: Tanabe Seiyaku Co., Ltd., Osaka, Japan

[21] Appl. No.: 729,841

[22] Filed: Jul. 12, 1991

Related U.S. Application Data

[62] Division of Ser. No. 329,408, Mar. 24, 1989, Pat. No. 5,068,112.

[30] Foreign Application Priority Data

Mar. 31, 1988 [JP] Japan .................. 63-80604

[51] Int. Cl.$^5$ .................................................. A61K 9/16
[52] U.S. Cl. .................................. 424/495; 424/451; 424/456; 424/480; 424/494
[58] Field of Search ................ 424/473, 494, 480, 495

[56] References Cited

U.S. PATENT DOCUMENTS

| | | | |
|---|---|---|---|
| 4,629,619 | 12/1986 | Lindahl | 424/15 |
| 4,663,147 | 5/1987 | DePrince | 424/467 |
| 4,666,702 | 5/1987 | Junginger | 424/497 |
| 4,769,027 | 9/1988 | Baker | 424/493 |
| 4,800,087 | 1/1989 | Mehta | 424/497 |
| 4,832,958 | 5/1989 | Baudier | 424/473 |

*Primary Examiner*—Thurman K. Page
*Assistant Examiner*—D. Gabrielle Phelan
*Attorney, Agent, or Firm*—Birch, Stewart, Kolasch & Birch

[57] ABSTRACT

Disclosed is a controlled release pharmaceutical preparation, comprising a core containing a pharmaceutically active ingredient, and a porous film of a hydrophobic polymeric substance or a hydrophobic polymeric substance and a hydrophilic polymeric substance, the core being coated with the porous film. Disclosed is also a method for producing the same. The controlled release pharmaceutical preparation of this invention posseses a desired dissolution rate by controlling the porosity of the porous film.

8 Claims, No Drawings

CONTROLLED RELEASE PHARMACEUTICAL PREPARATION AND METHOD FOR PRODUCING THE SAME

This application is a divisional of copending application Ser. No. 07/329,408, filed on Mar. 24, 1989, now U.S. Pat. No. 5,068,112, the entire contents of which are hereby incorporated by reference.

BACKGROUND OF THE INVENTION

This invention relates to a novel controlled release pharmaceutical preparation and a method for producing the same.

Heretofore, there has been known pharmaceutical preparations in which drug-containing cores are coated with compact films of hydrophobic polymeric substances.

Such preparations have advantages in that they have excellent water resistance, light resistance, humidity resistance, abrasion resistance, storage stability, etc.

However, a preparation having a compact film of a hydrophobic substance has disadvantages in that it has a slow releasing rate of the inner drug and also that the drug cannot be completely released.

In other words, release of a drug is a result of the difference in concentration or osmotic pressure between the inside and outside of the preparation which is created by the dissolution of the drug to a saturated concentration with the digestive fluids having penetrated into the inside through the film. However, since the compact film of a hydrophobic substance scarcely has open space, permeation of the fluid into the film is slow, and even when an osmotic pressure difference enough to release the drug may be created, the dissolution speed is not sufficient because of the small total area of the open space contributing to the release.

As to the method for solving this problem, there has been known a method in which particles of a water-soluble substance are embedded in the film of a hydrophobic polymeric substance so that the film may become porous in the digestive organs by dissolution and elimination of said water-soluble substance.

However, this method is still disadvantageous in that a special contrivance is required for embedding a water-soluble substance in the film, and that it is necessary to use various additives such as dispersing agents, plasticizers, anti-aggregating agents, etc. which make the recipe complicated. Moreover, even if the film may become porous in the digestive organs, its porosity will be affected by the particle size of the water-soluble substance or the degree of dispersion of said substance in the film, and therefore the porosity cannot be necessarily controlled accurately.

SUMMARY OF THE INVENTION

The present inventors have studied intensively in order to enable controlled release while maintaining the advantages of a preparation having a compact film of a hydrophobic polymeric substance such as great physical strength, good storage stability, etc. As a result, the inventors have succeeded in forming a porous film of a hydrophobic polymeric substance on the surface of a core, and also found that a controlled release pharmaceutical preparation having a desired dissolution rate can be obtained by controlling the porosity of the film.

Namely, according to the present invention, there is provided a controlled release pharmaceutical preparation comprising a core containing a pharmaceutical active ingredient, and a porous film of a hydrophobic polymeric substance, said core being coated with said porous film. Further, there is provided a method for producing said preparation.

DESCRIPTION OF THE PREFERRED EMBODIMENTS

In the present invention, the core to be coated with the porous film is not particularly limited to a specific form, but any of forms such as plain tablets, pills, granules, grains, etc. can be suitably used. However, it is preferable to use one granulated into granules, grains, etc., preferably one granulated into granules with an average particle size of about 300 μm to about 2000 μm, particularly about 500 μm to about 850 μm. The core of the present invention is not required to be hydrophobic, but both a water-soluble core and a water-insoluble core can be suitably used.

The core may contain a wide variety of excipients including diluents, binders, lubricants, anti-aggregating agents, buffers, which are conventionally used in this field of art. For example, as the diluents, sugars such as sucrose, lactose, mannitol, glucose, etc., starch, crystalline cellulose, calcium phosphate, calcium sulfate, calcium lactate, etc. may be included; as the binders, polyvinyl alcohol, polyacrylic acid, polymethacryic acid, polyvinyl pyrrolidone, glucose, sucrose, lactose, maltose, sorbitol, mannitol, hydroxyethyl cellulose, hydroxypropylmethyl cellulose, hydroxypropyl cellulose, polyethylene glycols, gum arabic, gelatin, agar, starch, etc. As the lubricants and anti-aggregating agents, talc, magnesium stearate, calcium stearate, colloidal silica, stearic acid, waxes, hardened oil, polyethylene glycols, sodium benzoate, sodium laurylsulfate, magnesium laurylsulfate, etc. may be included. Furhter, as the buffers, organic acids such as fumaric acid, succinic acid, citric acid, malic acid and their salts may be included.

The hydrophobic polymeric substance constituting the porous film is not particularly limited, provided that it has film forming ability, and is insoluble in water, but soluble in a water-miscible organic solvent. Examples of such a hydrophobic polymeric substance may include cellulose ether, cellulose ester, polyvinyl ester, acrylic acid type polymer having a quaternary ammonium-alkyl group, etc. Specifically, there may be included, for example, ethyl cellulose, butyl cellulose, cellulose acetate, cellulose propionate; polyvinyl acetate, polyvinyl butyrate; Eudragit RS (trade name of Röhm Pharma, chemical name: ethyl acrylate-methyl methacrylate-ethyl ammonium trimethyl chloride methacrylate copolymer), etc., and among them, preferable hydrophobic polymeric substances may include, for example, ethyl cellulose, butyl cellulose, cellulose acetate, cellulose propionate or Eudragit RS, etc. Among them, ethyl cellulose and cellulose acetate are particularly preferred, and most preferable is ethyl cellulose. Ethyl cellulose may be above all preferably a water-insoluble ethyl cellulose having, for example, an ethoxy content of about 40 to about 55%, particularly about 43% to about 51%, with a viscosity [viscosity measured at 5% ethyl cellulose concentration in toluene-ethanol (4:1) mixture at 25° C.] of about 4 to about 350 cP.

The porous film in the present invention may be, other than a porous film comprising only a hydrophobic polymeric substance, a porous film comprising a hydrophobic polymeric substance and a hydrophilic polymeric substance. In this case, as the hydrophilic polymeric substance, a water-soluble polymeric substance, an enteric polymeric substance, a gastric souble polymeric substance, and a both gastric and enteric polymeric substance may be suitably used.

Examples of the water-soluble polymeric substance, may include polysaccharides optionally having a sulfuric acid group such as pullulan, dextrin, alkali metal alginate, etc.; polysaccharides having a hydroxy-alkyl group or a carboxyalkyl group such as hydroxypropyl cellulose, hydroxypropylmethyl cellulose, carboxymethyl cellulose sodium, etc.; methyl cellulose, polyvinyl pyrrolidone, polyvinyl alcohol or polyethylene glycol, etc. may be included. Among them, more preferable water soluble polymeric substances may include hydroxypropyl cellulose or polyethylene glycol.

As the enteric polymeric substance, a polymeric substance having film forming ability and being soluble in water of pH 5 or higher may be used, including, for example, (1) carboxyalkyl cellulose, (2) a cellulose derivative having a monoester bond of a dibasic acid, (3) polyvinyl derivative having a monoester bond of dibasic acid, (4) maleic acid-vinyl copolymer or (5) acrylic acid type polymer, etc. Specific examples of (1) may include carboxymethyl cellulose; specific examples of (2) may include cellulose acetate phthalate, cellulose acetate succinate, methylcellulose phthalate, hydroxymethyl ethyl cellulose phthalate, hydroxypropylmethyl cellulose phthalate, hydroxypropylmethyl cellulose acetate succinate and the like; specific examples of (3) may include dibasic acid monoesters of vinyl polymers such as polyvinyl alcohol phthalate, polyvinyl butyrate phthalate, polyvinyl acetoacetal phthalate and the like; specific examples of (4) may include vinyl acetate-maleic anhydride copolymer, vinyl butyl ether-maleic anhydride copolymer, styrenemaleic acid monoester copolymer; and specific examples of (5) may include methyl acrylate-methacrylic acid copolymer, styrene-acrylic acid copolymer, methyl acrylate-methacrylic acid-octyl acrylate copolymer, Eudragit L and S (trade names of Rhom-Pharma, methacrylic acid-methyl methacrylate copolymer), etc. Among them, more preferable enteric polymeric substances are carboxylmethyl cellulose, hydroxypropyl methyl cellulose acetate succinate or Eudragit L.

Further, as the gastric soluble polymeric substance, any polymeric substance soluble in water having a pH 6 or lower and having film forming ability may be used, including, for example, (a) cellulose derivative having a mono- or di-substituted amino group, (b) a polyvinyl derivative having a mono- or di-substituted amino group, (c) an acrylic acid polymer having a mono-substituted amino group, etc. Specific examples of (a) may include benzylaminomethyl cellulose, diethylaminomethyl cellulose, piperidyl ethyl hydroxyethyl cellulose, cellulose acetate diethylamino acetate, etc. Specific examples of (b) may include vinyldiethylamine-vinyl acetate copolymer, vinylbenzylamine-vinyl acetate copolymer, polyvinyl acetaldiethylaminoacetate, vinylpiperidyl-acetoacetalvinyl acetate copolymer, polydiethyl aminomethyl styrene, etc., and specific examples of (c) may include Eudragit E (trade name of Rohm-Pharma, methyl methacrylate-butyl methacrylate-dimethylaminoethyl methacrylate copolymer), polydimethylaminoethyl methacrylate, etc. Among these, more preferable gastric soluble polymeric substances are polyvinyl acetal-diethylaminoacetate or Eudragit E.

As the both gastric soluble and enteric polymeric substance, a polymeric substance having film forming ability and being soluble in water of pH 4.5 or lower and water of pH 6 or higher may be used, including vinylpyridine-acrylic acid type copolymer, carboxymethyl polysaccharide having mono- or di-substituted amino group or polyvinyl amino acid type derivative. Specific examples of vinylpyridine-acrylic acid type copolymer may include 2-methyl-5-vinylpyridine/methyl methacrylate/ methacrylic acid copolymer, 2-methyl-5-vinylpyridine/ methyl acrylate/methacrylic acid copolymer, 2-vinyl-5-ethyl pyridine/methacrylic acid/styrene copolymer, 2-vinyl-5-ethyl pyridine/methacrylic acid/-methyl acrylate copolymer, 2-vinylpyridine/methacrylic acid/methyl acrylate copolymer, 2-vinylpyridine/-methacrylic acid/ acrylonitrile copolymer, etc. Specific examples of carboxymethyl polysaccharides having a mono- or di-substituted amino group may include carboxymethyl piperidyl starch, carboxymethyl benzylaminocellulose, etc., and specific examples of polyvinyl amino acid type derivative may include poly-2-(vinylphenyl)glycine, N-vinylglycine-styrene copolymer, etc.

The combination of the hydrophobic polymeric substance and the hydrophilic polymeric substance is not particularly limited, but as a preferable combination, a combination of a hydrophobic polymeric substance with a water soluble polymeric substance or an enteric polymeric substance may be included. As a particularly preferable combination, a combination of ethyl cellulose with hydroxypropylcellulose, carboxymethylethyl cellulose or hydroxypropylmethyl cellulose acetate succinate may be employed. The ratio of the hydrophobic polymeric substance to the hydrophilic polymeric substance should be desirably about 0.05 to 0.5 part by weight of the hydrophilic polymeric substance per 1 part by weight of the hydrophobic polymeric substance.

The porous film comprising the hydrophobic polymeric substance or a combination of the hydrophobic polymeric substance and the hydrophilic polymeric substance has generally an appearance like sponge, and has regular or irregular pores of microscopic sizes, which are mutually communicated to each other.

The porosity of the porous film is represented by the formula:

$$1 - \frac{\text{(total weight of film)/(total volume of film)}}{\text{(true specific gravity of film)}}$$

In general, the porosity should be appropriately made a value of about 0.4 to 0.9, particularly 0.5 to 0.85.

The thickness of the film may be controlled by the amount of the hydrophobic polymeric substance relative to the core, and it is desirable that the hydrophobic polymeric substance should be used in an amount within the range from about 3 to 100 W/W%, particularly about 5 to 50 w/w% based on the core. When the hydrophobic polymeric substance is used in combination with the hydrophilic polymeric substance, the total amount of both polymeric substances should be desirably within the range mentioned above.

In the preparation of the present invention, by controlling adequately the thickness and the porosity, it is possible to make a preparation having a desired dissolution rate. For example, when the pharmaceutically active ingredient contained in the core is a drug which is desired to exhibit a pharmaceutical effect within a short period of time after administration, it is preferred to make the film thinner and the porosity thereof greater, while in the case of a drug which is desired to be released persistently for a prolonged period of time, it is preferred to make the film thicker and the porosity thereof smaller.

As the pharmaceutically active ingredient to be contained in said core, any drug capable of oral administration may be available without any limitation. Examples of such pharmaceutically active ingredients may include vitamins, amino acids, peptides, chemotherapeutics, antibiotics, agents affecting respiratory organs, antitussive expectorants, antitumor agents, autonomic drugs, neuropsychotropic agents, muscle relaxants, drugs affecting digestive organs, antihistamic agents, antidotes, hypnotic sedatives, antiepileptics, antipyretic analgesic antiphlogistics, cardiotonics, antiarrhythmics, hypotensive diuretics, vasodilators, hypolipidemic agents, alimentary analeptics, anticoagulants, hepatics, blood sugar-lowering agents, hypotensive agents, etc.

The preparation of the present invention can be produced by spray coating a core containing a pharmaceutically active ingredient with a water-organic solvent mixture containing a hydrophobic polymeric substance or a mixture of a hydrophobic polymeric substance and a hydrophilic polymeric substance to form a porous film of said polymeric substance or substances on the surface of the core.

Preparation of a core can be practiced according to conventional methods as described in Remington's Pharmaceutical Science 17th ed., p.p. 1603 to 1632, p.p 1633 to 1643 (Mark Publishing Company, published in 1985). For example, the core can be prepared by mixing a pharmaceutical compound with a suitable excipient or excipients (i,e., diluents, binders, lubricants, etc.) and then granulating the mixture according to the wet extrusion granulating method, the rotating granulating method, the fluidized bed granulation method, etc. Alternatively, the core can be prepared according to the rotating granulation method, the pan coating method, the fluidized bed coating method, etc. in which a pharmaceutical compound or a mixture of the compound with an excipient or excipients is added little by little to inert carrier particles while spraying a solution of a binder dissolved in a suitable solvent such as water, lower alcohol (methanol, ethanol, propanol, isopropanol, butanol, etc.), lower alkanone (acetone, methyl ethyl ketone, etc.), chloroform, dichloromethane, dichloroethane or a mixture of these on the surface of inert carrier particles. In this case, as the inert carrier particles, for example, those prepared from sucrose, lactose, starch, crystalline cellulose, etc. may be suitably employed. Such carrier particles should preferably have an average particle size of about 300 μm to about 1500 μm.

In coating the core with a porous film, as the organic solvent which forms a solvent mixture together with water, any solvent which can dissolve the hydrophobic polymeric substance can be used without particular limitation, including, for example, lower alkanols such as methyl alcohol, ethyl alcohol, isopropyl alcohol, n-propyl alcohol, n-butyl alcohol, etc., lower alkanones such as acetone, methyl ethyl ketone, etc., acetonitrile and so on. Among these, a more preferable solvent is lower alkanols, and particularly preferable solvents are ethyl alcohol and isopropyl alcohol. The mixing ratio of water and the organic solvent is suitably variable within the range of 9 to 0.5 volumes of the organic solvent per one volume of water, and the porosity of the porous film comprising the hydrophobic polymeric substance or the combination of the hydrophobic polymeric substance and the hydrophilic polymeric substance can readily be controlled by changing said ratio. The porosity of the porous film, as a general rule, becomes greater as the ratio of water in the water-organic solvent mixture is increased and smaller when the ratio of the organic solvent is increased.

The concentration of the hydrophobic polymeric substance in the water-organic solvent mixture should be preferably about 2 to 30 w/w%. Also, when a hydrophobic polymeric substance is used in combination with a hydrophilic polymeric substance, the total concentration of the both polymeric substances should be preferably within the above range.

Spray coating can be practiced according to conventional coating methods. For example, it can be practiced easily by dissolving a hydrophobic polymeric substance or a combination of a hydrophobic polymeric substance and a hydrophilic polymeric substance in a water-organic solvent mixture, and spraying the resultant coating solution on the surface of a core according to the fluidized bed coating method, the pan coating method, etc. For example, according to the pan coating method, it is possible to practice the method by placing cores in a coating pan, spraying a water-organic solvent mixture containing a hydrophobic polymeric substance or a combination of a hydrophobic polymeric substance and a hydrophilic polymeric substance through a nozzle of a spray gun while rotating said coating pan, and then drying the coating.

At this time, if desired, talc, titanium dioxide, etc. may be also added as the anti-aggregating agent.

The thus-obtained pharmaceutical preparation of the present invention may be administered as such or said preparation can be also administered in the form of filled capsules when the preparation is in shape of granules.

The controlled release pharmaceutical preparation of the present invention is characterized in that it shows rapid stand-up of release. This is because, since the film is porous, digestive fluids penetrate into the inside of the preparation and dissolve the pharmaceutically active ingredient from the time immediately after administration. Besides, the preparation of the present invention is characterized in that the release rate can be readily controlled by changing the porosity of the film. For example, in the case where it is necessary to reduce the variation of blood level of the pharmaceutically active ingredient because the minimum therapeutically effective blood level of said active ingredient is close to the toxic blood level thereof, it is possible to minimize the variation between the highest and lowest blood concentration thereof by making the porosity of the film smaller in order to exhibit the therapeutic effect of the active ingredient while keeping the blood level thereof lower than the toxic level. Further, in the case where the pharmaceutically active ingredient is desired to impart long-lasting action, it is possible to release the active ingredient at a constant rate for a prolonged period of time by making the porosity of the film smaller. On the other hand, in the case where the active ingredient is desired to show rapid action, it is possible to release the active ingredient from the time immediately after administration by making the porosity of the film greater.

Moreover, the pharmaceutical preparation having a porous film comprising a hydrophobic polymeric substance and a hydrophilic polymeric substance is effective to dissolve and release the pharmaceutical ingredient more quickly and within a shorter period of time after administration because the porosity of the film itself becomes further greater by dissolution of the hydrophilic substance constituting a part of the porous film.

Besides, the preparation of the present invention is not inferior at all with respect to humidity resistance, light shielding property, water resistnce, abrasion resistance as compared with the known preparation having a compact film of a hydrophobic polymeric substance.

As described above, the preparation of the present invention is excellent in release control and at the same time, maintains the advantages possessed by the preparation of the prior art as such.

EXPERIMENTAL EXAMPLES (1) Production of preparation:

One kg of Nonpareil (trade name of spherical granules of sucrose, manufactured by Freund) with particle sizes of 710 to 840 μm was placed and tumbled in a centrifugal fluidizing granulator (CF-360 EX Model, manufactured by Freund), and thereto was gradually added 1 kg of dilthiazem hydrochloride powder while spraying a water-ethanol solution (weight ratio=3:1) containing 400 g of sucrose to cover it around Nonpareil. Subsequently, the dilthiazem hydrochloride granules obtained were sprayed with a coating solution of 300 g of ethyl cellulose (ethoxy content: 49.6%) dissolved in 2.7 kg of a water-ethanol mixture (weight ratio=3:7, 2:8 or 1.5:8.5) while blowing warm air. By drying after spraying, dilthiazem hydrochloride containing preparations having porous ethyl cellulose films with different porosities, respectively, were obtained.

(2) Comparison of releasing rate:

For the respective preparations obtained as described above, the dissolution tests were practiced according to the dissolution test standard of the Paddle method specified in the 11th revised Japanese Pharmacopoeia.

(3) Results:

The dissolution percentage of the active ingredient (dilthiazem hydrochloride) is as shown in Table 1.

TABLE 1

| Preparation (*1) | Porosity (*2) | dissolution percentage (%) | | |
|---|---|---|---|---|
| | | 4 hours | 10 hours | 24 hours |
| A | 0.83 | 34 | 77 | 100 |
| B | 0.54 | 20 | 53 | 86 |
| C | 0.42 | 17 | 34 | 52 |

(note):
(*1) A–C show the following preparations:
A: preparation obtained by use of a water-ethanol mixture (3:7) as the solvent of the coating solution;
B: preparation obtained by use of a water-ethanol mixture (2:8) as the solvent of the coating solution;
C: preparation obtained by use of a water-ethanol mixture (1.5:8.5)) as the solvent of the coating solution;
(*2): porosity was calculated according to the above formula (I).

As is apparent from the above Table 1, it can be seen that as the ratio of water in the water-ethanol mixture becomes smaller, the porosity of the film becomes smaller and a period of time to be required for dissolving 100% of the active ingredient become longer.

EXAMPLE 1

500 g of Nonpareil with particle sizes of 710 to 840 μm were placed and tumbled in a centrifugal fluidizing granulator, and to this was gradually added 1 kg of theophylline (chemical name: 3,7-dihydro-1,3-dimethyl-1H-purine-2,6-dione) fine powder while spraying a solution of 270 g of sucrose dissolved in 145 ml of water to cover it around Nonpareil. Subsequently, 1 kg of the theophylline granules obtained was placed and tumbled in a centrifugal fluidizing granulator, and to this was sprayed a solution of 90 g of ethyl cellulose and 10 g of hydroxypropyl cellulose dissolved in 1.9 kg of a water-ethanol (3:7) mixture while blowing warm air. Subsequently, after drying, 1.1 kg of theophylline granules coated with a porous ethylcellulose-hydroxypropylcellulose film were obtained.

The preparation obtained had a porous film of a porosity of 0.81.

EXAMPLE 2

One kg of Nonpareil with particle sizes of 710 to 840 μm was placed and tumbled in a centrifugal fluidizing granulator, and to this was added gradually 1 kg of sodium salicylate powder while spraying 800 g of a water-ethanol mixture containing 400 g of sucrose to have it attached around Nonpareil. Subsequently, 500 g of the sodium salicylate granules obtained were placed in a fluidized bed coater and, under blow rotation with blowing of air, a mixture of 100 g of ethyl cellulose dissolved in 900 g of a water-ethanol (2:8) mixture added with 50 g of talc was sprayed thereon while blowing warm air. By drying after spraying, 600 g of sodium salicylate granules coated with a porous ethyl cellulose film were obtained. The preparation obtained had a porous film of a porosity of 0.68.

EXAMPLE 3

1.33 kg of Nonpareil with particle sizes of 500 to 710 um were placed and tumbled in a centrifugal fluidizing granulator, and to this was gradually added a mixture of 1 kg of (+)-(2S,3S)-3-acetoxy-8-chloro-5-[2-(dimethylamino)ethyl]-2,3-dihydro-2-(4-methoxy maleate fine powder and 1.67 g of succinic acid while spraying a solution of 652 g of sucrose dissolved in 1,957 g of a water-ethanol (3:1) mixture to cover it around Nonpareil. Subsequently, 2 kg of the granules obtained were placed and tumbled in a centrifugal fluidizing granulator, and a solution of 190 g of ethyl cellulose and 10 g of hydroxypropyl cellulose dissolved in 1.8 kg of a water-ethanol (3:7) mixture was sprayed thereon, while blowing warm air. Then, after drying, 2.2 kg of granules coated with a porous ethyl cellulose-hydroxypropyl cellulose film wereobtained.

The preparation obtained had a porous film of a porosity of 0.85.

EXAMPLE 4

A mixture of 300 g of dilthiazem hydrochloride, 611 g of lactose and 150 g of corn starch was kneaded with 30 g of polyvinyl pyrrolidone and 100 ml of water, and the particles obtained were classified to obtain granules for tabletting. Then, to the granules were added 8 g of magnesium stearate, and the mixture was tabletted by a rotary system tabletting machine (RT F-9-2 Model, manufactured by Kikusui Seisakusho) to obtain tablets of 8 mm in diameter. The dilthiazem hydrochloride containing tablets obtained (500 g) were placed in a coating pan, and a water-ethanol (3:7) mixture containing 5 W/W% of ethyl cellulose was sprayed thereon at room temperature. Subsequently, after drying, tablets coated with a porous ethyl cellulose film were obtained.

The preparaton obtained had a porous film of a porosity of 0.67.

EXAMPLE 5

500 g of theophylline granules (cores) obtained in the same manner as in Example 1 were placed in a centrifugal fluidizing granulator, and a solution of 50 g of ethyl cellulose dissolved in a water-isopropanol mixture (4:6) was sprayed thereon while blowing warm air. Subsequently, after drying, about 500 g of granules coated with a porous ethyl cellulose film were obtained.

The preparation obtained had a porous film of a porosity of 0.78.

EXAMPLE 6

500 g of sodium salicylate granules (cores) obtained in the same manner as in Example 2 were placed in a fluidized bed coating device. 50 g of talc were added to a solution of 100 g of cellulose acetate in 900 g of a mixture of water-acetone (2:8), and the mixture was sprayed on the surface of granules while blowing warm air. By drying after spraying, 600 g of granules coated with a porous cellulose acetate film were obtained.

The granules obtained had a porous film of a porosity of 0.74.

EXAMPLE 7

Example 1 was repeated except for using 100 g of cellulose acetate butyrate in place of cellulose acetate to obtain 600 g of granules coated with a porous cellulose acetate butyrate film.

The preparation obtained had a porous film of a porosity of 0.78.

EXAMPLES 8

One kg of the granules (cores) obtained in the same manner as in Example 3 was placed and tumbled in a centrifugal fluidizing granulator, and a solution of 95 g of ethyl cellulose and 5 g of polyvinyl pyrrolidone dissolved in 900 g of a water-ethanol (3:7) mixture was sprayed thereon while blowing warm air. By drying after spraying, 1.1 kg of granules coated with a porous ethyl cellulose-polyvinyl pyrrolidone film were obtained.

The preparation obtained had a porous film of a porosity of 0.81.

EXAMPLE 9

Example 8 was repeated except for using 95 g ethyl cellulose and 5 g of polyethylene glycol to give 1.1 kg of granules coated with a porous ethyl cellulose-polyethylene glycol film.

The preparation obtained had a porous film of a porosity of 0.79.

EXAMPLE 10

Example 8 was repeated except for using 95 g ethyl cellulose and 5 g of methyl cellulose to give 1.1 kg of granules coated with a porous ethyl cellulose-methylcellulose film.

The preparation obtained had a porous film of a porosity of 0.82.

EXAMPLE 11

Example 8 was repeated except for using 95 g ethyl cellulose and 5 g of hydroxypropylmethyl cellulose to give 1.1 kg of granules coated with a porous ethyl cellulose-hydroxypropylmethyl cellulose film.

The preparation obtained had a porous film of a porosity of 0.76.

EXAMPLE 12

Example 8 was repeated except for using 95 g ethyl cellulose and 5 g of hydroxypropyl cellulose acetate succinate to give 1.1 kg of granules coated with a porous ethyl cellulose-hydroxypropyl cellulose acetate succinate film.

The preparation obtained had a porous film of a porosity of 0.84.

EXAMPLE 13

Example 8 was repeated except for using 95 g ethyl cellulose and 5 g of Eudragit L to give 1.1 kg of granules coated with a porous ethyl cellulose-Eudragit L film.

The preparation obtained had a porous film of a porosity of 0.79.

We claim:

1. A controlled release pharmaceutical preparation comprising:
   (a) a core containing a pharmaceutically active ingredient; and
   (b) a porous cellulose film formed on the surface of said core by spraying a water-organic solvent mixture containing ethyl cellulose or a mixture of ethyl cellulose and hydroxypropyl cellulose, said porous cellulose film having a porosity of about 0.4 to 0.9 calculated according to the formula:

$$1 - \frac{\text{(total weight of film)/(total volume of film)}}{\text{(true specific gravity of film)}}.$$

2. The preparation according to claim 1, wherein said porous film has a porosity of about 0.5 to 0.85.

3. The preparation according to claim 1, wherein said porous film comprises ethyl cellulose.

4. The preparation according to claim 1, wherein said porous film comprises ethyl cellulose and hydroxypropyl cellulose.

5. The preparation according to claim 4, wherein said porous film comprises 0.05 to 0.5 part by weight of said hydroxypropyl cellulose per 1 part by weight of said ethyl cellulose.

6. A method of producing a controlled release pharmaceutical preparation which comprises spray-coating a water-organic solvent mixture containing ethyl cellulose or a mixture of ethyl cellulose and hydroxypropyl cellulose onto the surface of a core containing a pharmaceutically active ingredient to produce a porous cellulose film on said core, said porous cellulose film having a porosity of about 0.4 to 0.9 calculated according to the formula:

$$1 - \frac{\text{(total weight of film)/(total volume of film)}}{\text{(true specific gravity of film)}}.$$

7. The preparation according to claim 1, wherein said organic solvent is ethanol.

8. The method according to claim 6, wherein said organic solvent is ethanol.

* * * * *